(12) United States Patent
Sheynblat et al.

(10) Patent No.: US 11,659,996 B2
(45) Date of Patent: May 30, 2023

(54) MULTI-SENSOR DATA COLLECTION AND/OR PROCESSING

(71) Applicant: QUALCOMM Incorporated, San Diego, CA (US)

(72) Inventors: Leonid Sheynblat, Hillsborough, CA (US); Thomas Wolf, Mountain View, CA (US); Alexander Hodisan, Haifa (IL)

(73) Assignee: QUALCOMM Incorporated, San Diego, CA (US)

( * ) Notice: Subject to any disclaimer, the term of this patent is extended or adjusted under 35 U.S.C. 154(b) by 165 days.

(21) Appl. No.: 16/534,129

(22) Filed: Aug. 7, 2019

(65) Prior Publication Data
US 2020/0029814 A1 Jan. 30, 2020

Related U.S. Application Data

(60) Continuation of application No. 14/139,346, filed on Dec. 23, 2013, now abandoned, which is a division of
(Continued)

(51) Int. Cl.
*A61B 5/00* (2006.01)
*G06F 1/3206* (2019.01)
(Continued)

(52) U.S. Cl.
CPC ............ *A61B 5/0024* (2013.01); *A61B 5/021* (2013.01); *A61B 5/024* (2013.01); *A61B 5/0205* (2013.01);
(Continued)

(58) Field of Classification Search
CPC ....... A61B 5/0024; A61B 5/021; A61B 5/024; A61B 5/0205; G06F 1/1694; G06F 1/3206; G01C 21/00; G01C 21/16
See application file for complete search history.

(56) References Cited

U.S. PATENT DOCUMENTS 3,442,140 A 5/1969 Frank
4,908,767 A 3/1990 Scholl et al.
(Continued)

FOREIGN PATENT DOCUMENTS

CN 1212085 A 3/1999
CN 1452414 A 10/2003
(Continued)

OTHER PUBLICATIONS

E. Nebot, S. Sukkarieh and H. Durrant-Whyte, "Inertial navigation aided with GPS information," Proceedings Fourth Annual Conference on Mechatronics and Machine Vision in Practice, 1997, pp. 169-174, doi: 10.1109/MMVIP.1997.625317. (Year: 1997).*
(Continued)

*Primary Examiner* — Evangeline Barr
(74) *Attorney, Agent, or Firm* — Qualcomm Incorporated

(57) ABSTRACT

The subject matter disclosed herein relates to the control and utilization of multiple sensors within a device. For an example, motion of a device may be detected in response to receipt of a signal from a first sensor disposed in the device, and a power state of a second sensor also disposed in the device may be changed in response to detected motion.

28 Claims, 11 Drawing Sheets

Related U.S. Application Data application No. 12/054,303, filed on Mar. 24, 2008, now Pat. No. 8,718,938.

(60) Provisional application No. 60/914,716, filed on Apr. 27, 2007, provisional application No. 60/909,380, filed on Mar. 30, 2007, provisional application No. 60/896,795, filed on Mar. 23, 2007.

(51) Int. Cl.
| | |
|---|---|
| G01C 19/02 | (2006.01) |
| A61B 5/021 | (2006.01) |
| A61B 5/024 | (2006.01) |
| A61B 5/0205 | (2006.01) |
| G06F 1/16 | (2006.01) |
| G06F 1/3287 | (2019.01) |
| G01C 21/16 | (2006.01) |
| G05F 1/70 | (2006.01) |

(52) U.S. Cl.
CPC .......... *A61B 5/6898* (2013.01); *G01C 19/02* (2013.01); *G01C 21/188* (2020.08); *G05F 1/70* (2013.01); *G06F 1/1694* (2013.01); *G06F 1/3206* (2013.01); *G06F 1/3287* (2013.01); *A61B 2560/0209* (2013.01); *G06F 2200/1637* (2013.01); *Y02D 10/00* (2018.01)

(56) References Cited

U.S. PATENT DOCUMENTS

| | | | |
|---|---|---|---|
| 5,404,307 A | 4/1995 | Odagawa | |
| 5,570,304 A | 10/1996 | Mark et al. | |
| 5,674,127 A | 10/1997 | Horstmann et al. | |
| 5,703,623 A * | 12/1997 | Hall ...................... | G06F 3/0346 345/157 |
| 5,859,693 A | 1/1999 | Dunne et al. | |
| 5,889,474 A | 3/1999 | Ladue | |
| 5,952,959 A | 9/1999 | Norris | |
| 6,052,646 A | 4/2000 | Kirkhart et al. | |
| 6,083,353 A | 7/2000 | Alexander, Jr. | |
| 6,282,495 B1 | 8/2001 | Kirkhart et al. | |
| 6,282,496 B1 | 8/2001 | Chowdhary | |
| 6,408,251 B1 | 6/2002 | Azuma | |
| 6,421,622 B1 | 7/2002 | Horton et al. | |
| 6,452,494 B1 | 9/2002 | Harrison | |
| 6,622,091 B2 | 9/2003 | Perlmutter et al. | |
| 6,734,845 B1 | 5/2004 | Nielsen et al. | |
| 6,842,991 B2 | 1/2005 | Levi et al. | |
| 7,072,668 B2 | 7/2006 | Chou et al. | |
| 7,155,837 B2 | 1/2007 | Cho et al. | |
| 7,171,334 B2 | 1/2007 | Gassner et al. | |
| 7,188,042 B2 | 3/2007 | Havens | |
| 7,197,921 B2 | 4/2007 | Kramer et al. | |
| 7,248,059 B1 | 7/2007 | Ochoco et al. | |
| 7,269,095 B2 | 9/2007 | Chamberlain et al. | |
| 7,330,729 B2 | 2/2008 | Niwa et al. | |
| 7,478,108 B2 | 1/2009 | Townsend et al. | |
| 7,543,169 B2 | 6/2009 | Yamaji et al. | |
| 7,664,463 B2 | 2/2010 | Ben et al. | |
| 7,923,998 B2 | 4/2011 | Hammerschmidt et al. | |
| 8,666,460 B2 | 3/2014 | Weinberg et al. | |
| 8,718,938 B2 | 5/2014 | Wolf et al. | |
| 9,220,410 B2 | 12/2015 | Sheynblat et al. | |
| 2001/0049471 A1 | 12/2001 | Suzuki et al. | |
| 2002/0021278 A1 | 2/2002 | Hinckley et al. | |
| 2003/0114980 A1 | 6/2003 | Klausner et al. | |
| 2005/0034373 A1 | 2/2005 | Belmond et al. | |
| 2005/0168586 A1 | 8/2005 | Tsubusaki | |
| 2006/0113960 A1 | 6/2006 | Thulesius et al. | |
| 2006/0129308 A1 * | 6/2006 | Kates ..................... | A61H 3/066 701/532 |
| 2006/0169907 A1 | 8/2006 | Shinden | |
| 2006/0176149 A1 | 8/2006 | Douglas | |
| 2006/0230108 A1 | 10/2006 | Tatsuta et al. | |
| 2007/0004969 A1 | 1/2007 | Kong et al. | |
| 2007/0024581 A1 | 2/2007 | Kim et al. | |
| 2007/0033068 A1 * | 2/2007 | Rao ........................ | G16H 40/40 705/2 |
| 2007/0208544 A1 * | 9/2007 | Kulach ............... | G01C 22/006 702/158 |
| 2007/0233382 A1 | 10/2007 | Preston | |
| 2007/0241888 A1 | 10/2007 | Mantovani et al. | |
| 2008/0001735 A1 * | 1/2008 | Tran ..................... | A61B 5/6803 340/539.22 |
| 2008/0058032 A1 | 3/2008 | Yamaji et al. | |
| 2008/0174550 A1 | 7/2008 | Laurila et al. | |
| 2015/0173617 A1 | 6/2015 | Sheynblat | |

FOREIGN PATENT DOCUMENTS

| | | |
|---|---|---|
| CN | 1476585 A | 2/2004 |
| CN | 1543594 A | 11/2004 |
| CN | 1639542 A | 7/2005 |
| CN | 1813192 A | 8/2006 |
| CN | 1822791 A | 8/2006 |
| CN | 1826250 A | 8/2006 |
| CN | 1897552 A | 1/2007 |
| CN | 1910428 A | 2/2007 |
| CN | 1912545 A | 2/2007 |
| CN | 1914517 A | 2/2007 |
| DE | 4218658 A1 | 12/1992 |
| EP | 0555586 A1 | 8/1993 |
| EP | 1041360 A2 | 10/2000 |
| EP | 1132713 A1 | 9/2001 |
| EP | 1574875 A1 | 9/2005 |
| EP | 1755098 A2 | 2/2007 |
| JP | 2000283801 A | 10/2000 |
| JP | 2001344352 A | 12/2001 |
| JP | 2003287428 A | 10/2003 |
| JP | 2005223431 A | 8/2005 |
| JP | 2005284596 A | 10/2005 |
| JP | 2006208308 A | 8/2006 |
| JP | 2007015502 A | 1/2007 |
| JP | 2007057510 A | 3/2007 |
| KR | 100571795 B1 | 4/2006 |
| WO | WO-98013966 | 4/1998 |
| WO | WO-9910709 A2 | 3/1999 |
| WO | WO-2005004502 A2 | 1/2005 |
| WO | WO-2006070272 A2 | 7/2006 |
| WO | 2007134664 A1 | 11/2007 |
| WO | WO-2008095225 A1 | 8/2008 |

OTHER PUBLICATIONS

Benbasat A.Y., et al., "An Automated Framwork for Power-Efficient Detection in Embedded Sensor Systems", Massachusetts Institute of Technology, Feb. 2007, 200 Pages.

Benbasat A.Y., et al., "Design of a Real-Time Adaptive Power Optimal Sensor System", IEEE, Sensor, 2004, 4 Pages.

Benbasat A.Y., et al., "Groggy Wakeup—Automated Generation of Power-Efficient Detection Hierarchies for Wearable Sensors", In Proceedings of the 4th International Workshop on Wearable and Implantable Body Sensor Networks (BSN 2007), 2007, pp. 59-64.

European Search Report—EP12004708—Search Authority—The Hague—dated Jul. 3, 2014.

Farella E., et al., "Design and Implementation of WiMoCA Node for a Body Area Wireless Sensor Network", Proceedings of the 2005 Systems Communications (ICW'05), Jan. 2005, 7 Pages.

International Preliminary Reporton Patentability—PCT/US2008/058060, The International Bureau of WIPO—Geneva, Switzerland, dated Sep. 29, 2009.

International Search Report and Written Opinion—PCT/US2008/058060, International Search Authority—European Patent Office—dated Oct. 30, 2008.

Otto C., "An Implementation of a Wireless Body Area Network for Ambulatory Health Monitoring", Huntsville, Alabama, 2006, 126 Pages.

Correia J.H., et al., "A Microinstrumentation System for Industrial Applications," ISIE '97 Proceeding of the IEEE International Symposium on Industrial Electronics, Jul. 1997, 5 pages.

(56) References Cited

OTHER PUBLICATIONS

Mason A.J., "Portable Wireless Multi-Sensor Microsystems for Environmental Monitoring," 2000, 185 pages.
Najafi K., "Low-Power Micromachined Microsystems," Proceedings of the 2000 International Symposium on Low Power Electronics and Design, Jul. 2000, 8 pages.
European Search Report—EP19194594—Search Authority—The Hague—dated Apr. 22, 2020.
Roetenberg, D. et "Compensation of Magnetic Disturbances Improves Inertial and Magnetic Sensing of Human Body Segment Orientation", IEEE Transactions on Neural Systems and Rehabilitation Engineering, vol. 13, No. 3, Sep. 2005, pp. 395-405.

* cited by examiner

MULTI-SENSOR DATA COLLECTION AND/OR PROCESSING

CLAIM OF PRIORITY UNDER 35 U.S.C. § 119

The present application is a continuation application of and claims priority to, U.S. patent application Ser. No. 14/139,346, filed Dec. 23, 2013, and entitled "MULTI-SENSOR DATA COLLECTION AND/OR PROCESSING", which is a divisional application of and claims priority to, U.S. application Ser. No. 12/054,303, filed Mar. 24, 2008, and entitled "MULTI-SENSOR DATA COLLECTION AND/OR PROCESSING," which claims the benefit of and priority to provisional U.S. Application No. 60/896,795, entitled, "MULTI-SENSOR MEASUREMENT PROCESSING UNIT" filed on Mar. 23, 2007, to provisional U.S. Application No. 60/909,380, entitled, "MULTI-SENSOR MEASUREMENT PROCESSING UNIT" filed on Mar. 30, 2007, and to provisional U.S. Application No. 60/914,716, entitled "MULTI-SENSOR MEASUREMENT PROCESSING UNIT" filed on Apr. 27, 2007, which is assigned to the assignee hereof and which is expressly incorporated herein by reference.

BACKGROUND

Field

The subject matter disclosed herein relates to the collection and/or processing of sensor data from multiple sensors.

Information

A variety of sensors are available to support a number of applications in today's market. These sensors may convert physical phenomena into analog and/or electrical signals. Such sensors may include, for example, a barometric pressure sensor. A barometric pressure sensor may be used to measure atmospheric pressure. Applications for the barometric pressure sensor may include determining altitude. Other applications may include observing atmospheric pressure as it relates to weather conditions.

Another sensor type may include an accelerometer. An accelerometer may sense the direction of gravity and any other force experienced by the sensor. The accelerometer may be used to sense linear and/or angular movement, and may also be used, for example, to measure tilt and/or roll.

Yet another sensor type may include a gyroscope which measures the Coriolis effect and may be used in applications measuring heading changes or in measuring rate of rotation. Gyroscopes have, for example, important applications in the field of navigation.

Another type of sensor may include a magnetic field sensor that may measure the strength of a magnetic field and, correspondingly, the direction of a magnetic field. A compass is an example of a magnetic field sensor. The compass may find use in determining absolute heading in car and pedestrian navigation applications.

Biometric sensors represent another type of sensors that may have a variety of possible applications. Some examples of biometric sensors may include heart rate monitors, blood pressure monitors, fingerprint detection, touch (heptic) sensors, blood sugar (glucose) level measuring sensors, etc.

The above sensors, as well as other possible sensors not listed, may be utilized individually or may be used in combination with other sensors, depending on the particular application. For example, in navigation applications, accelerometers, gyroscopes, geomagnetic sensors, and pressure sensors may be utilized to provide adequate degrees of observability. For one example, the accelerometer and gyroscope may provide six axes of observability (x, y, z, τ, φ, ψ). As mentioned above, the accelerometer may sense linear motion (translation in any plane, such as a local horizontal plane). This translation may be measured with reference to at least one axis. The accelerometer may also provide a measure of an object's tilt (roll or pitch). Thus, with the accelerometer, an object's motion in Cartesian coordinate space (x, y, z) may be sensed, and the direction of gravity may be sensed to estimate an object's roll and pitch. The gyroscope may be used to measure the rate of rotation about (x, y, z), i.e., roll (τ) and pitch (φ) and yaw, which may also be referred to as azimuth or "heading" (ψ).

Navigational applications are merely one example of how more than one sensor type may be utilized in combination to provide multi-axes measurement capabilities. The utilization of multiple sensors to perform measurements may present a number of challenges to users of these devices. Such challenges may include, for example, size, cost, interfaces, connectivity, and/or power consumption of the multiple sensors.

SUMMARY

In one aspect, motion of a device may be detected in response to receipt of a signal from a first sensor disposed in the device, and a power state of a second sensor also disposed in the device may be changed in response to detected motion.

BRIEF DESCRIPTION OF THE FIGURES

Non-limiting and non-exhaustive examples will be described with reference to the following figures, wherein like reference numerals refer to like parts throughout the various figures.

DETAILED DESCRIPTION

Figure 1:
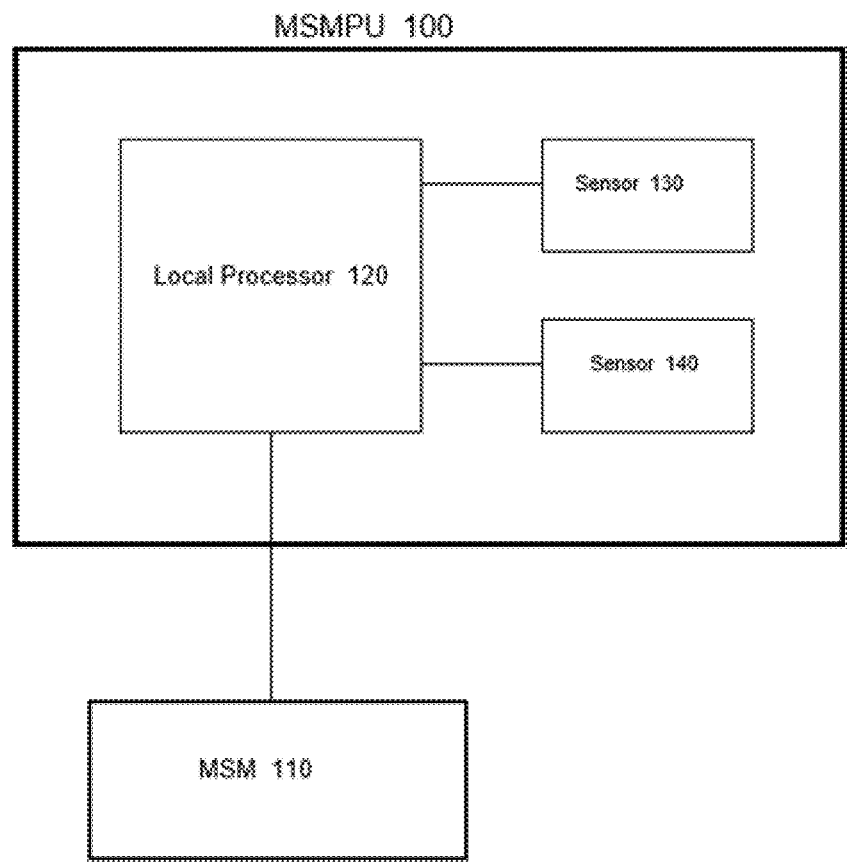
FIG. 1 is a block diagram of an example multi-sensor measurement processing unit (MSMPU).

Reference throughout this specification to "one example", "one feature", "an example" or "a feature" means that a particular feature, structure, or characteristic described in connection with the feature and/or example is included in at least one feature and/or example of claimed subject matter. Thus, the appearances of the phrase "in one example", "an example", "in one feature" or "a feature" in various places throughout this specification are not necessarily all referring to the same feature and/or example. Furthermore, the particular features, structures, or characteristics may be combined in one or more examples and/or features.

The methodologies described herein may be implemented by various means depending upon applications according to particular examples. For example, such methodologies may be implemented in hardware, firmware, software, and/or combinations thereof. In a hardware implementation, for example, a processing unit may be implemented within one or more application specific integrated circuits (ASICs), digital signal processors (DSPs), digital signal processing devices (DSPDs), programmable logic devices (PLDs), field programmable gate arrays (FPGAs), processors, controllers, micro-controllers, microprocessors, electronic devices, other devices units designed to perform the functions described herein, and/or combinations thereof.

"Instructions" as referred to herein relate to expressions which represent one or more logical operations. For example, instructions may be "machine-readable" by being interpretable by a machine for executing one or more operations on one or more data objects. However, this is merely an example of instructions and claimed subject matter is not limited in this respect. In another example, instructions as referred to herein may relate to encoded commands which are executable by a processing circuit having a command set which includes the encoded commands. Such an instruction may be encoded in the form of a machine language understood by the processing circuit. Again, these are merely examples of an instruction and claimed subject matter is not limited in this respect.

"Storage medium" as referred to herein relates to media capable of maintaining expressions which are perceivable by one or more machines. For example, a storage medium may comprise one or more storage devices for storing machine-readable instructions and/or information. Such storage devices may comprise any one of several media types including, for example, magnetic, optical or semiconductor storage media. Such storage devices may also comprise any type of long term, short term, volatile or non-volatile memory devices. However, these are merely examples of a storage medium, and claimed subject matter is not limited in these respects.

Unless specifically stated otherwise, as apparent from the following discussion, it is appreciated that throughout this specification discussions utilizing terms such as "processing," "computing," "calculating," "selecting," "forming," "enabling," "inhibiting," "locating," "terminating," "identifying," "initiating," "detecting," "obtaining," "hosting," "maintaining," "representing," "estimating," "receiving," "transmitting," "determining" and/or the like refer to the actions and/or processes that may be performed by a computing platform, such as a computer or a similar electronic computing device, that manipulates and/or transforms data represented as physical electronic and/or magnetic quantities and/or other physical quantities within the computing platform's processors, memories, registers, and/or other information storage, transmission, reception and/or display devices. Such actions and/or processes may be executed by a computing platform under the control of machine-readable instructions stored in a storage medium, for example. Such machine-readable instructions may comprise, for example, software or firmware stored in a storage medium included as part of a computing platform (e.g., included as part of a processing circuit or external to such a processing circuit). Further, unless specifically stated otherwise, processes described herein, with reference to flow diagrams or otherwise, may also be executed and/or controlled, in whole or in part, by such a computing platform.

Wireless communication techniques described herein may be in connection with various wireless communication networks such as a wireless wide area network (WWAN), a wireless local area network (WLAN), a wireless personal area network (WPAN), and so on. The term "network" and "system" may be used interchangeably herein. A WWAN may be a Code Division Multiple Access (CDMA) network, a Time Division Multiple Access (TDMA) network, a Frequency Division Multiple Access (FDMA) network, an Orthogonal Frequency Division Multiple Access (OFDMA) network, a Single-Carrier Frequency Division Multiple Access (SC-FDMA) network, or any combination of the above networks, and so on. A CDMA network may implement one or more radio access technologies (RATs) such as cdma2000, Wideband-CDMA (W-CDMA), to name just a few radio technologies. Here, cdma2000 may include technologies implemented according to IS-95, IS-2000, and IS-856 standards. A TDMA network may implement Global System for Mobile Communications (GSM), Digital Advanced Mobile Phone System (D-AMPS), or some other RAT. GSM and W-CDMA are described in documents from a consortium named "3rd Generation Partnership Project" (3GPP). Cdma2000 is described in documents from a consortium named "3rd Generation Partnership Project 2" (3GPP2). 3GPP and 3GPP2 documents are publicly available. A WLAN may comprise an IEEE 802.11x network, and a WPAN may comprise a Bluetooth network, an IEEE 802.15x, for example. Wireless communication implementations described herein may also be used in connection with any combination of WWAN, WLAN and/or WPAN.

In one example, a device and/or system may estimate its location based, at least in part, on signals received from satellites. In particular, such a device and/or system may obtain "pseudorange" measurements comprising approximations of distances between associated satellites and a navigation satellite receiver. In a particular example, such a pseudorange may be determined at a receiver that is capable of processing signals from one or more satellites as part of a Satellite Positioning System (SPS). Such an SPS may comprise, for example, a Global Positioning System (GPS), Galileo, Glonass, to name a few, or any SPS developed in the future. To determine its position, a satellite navigation receiver may obtain pseudorange measurements to three or more satellites as well as their positions at time of transmitting. Knowing the satellite's orbital parameters, these satellite positions can be calculated for any point in time. A pseudorange measurement may then be determined based, at least in part, on the time a signal travels from a satellite to the receiver, multiplied by the speed of light. While techniques described herein may be provided as implementations of location determination in a GPS, EGNOS, WAAS, Glonass and/or Galileo types of SPS as specific illustrations, it should be understood that these techniques may also apply to other types of SPS, and that claimed subject matter is not limited in this respect.

Techniques described herein may be used with any one or more of several SPS, including the aforementioned SPS, for example. Furthermore, such techniques may be used with positioning determination systems that utilize pseudolites or a combination of satellites and pseudolites. Pseudolites may comprise ground-based transmitters that broadcast a PRN code or other ranging code (e.g., similar to a GPS or CDMA cellular signal) modulated on an L-band (or other frequency) carrier signal, which may be synchronized with GPS time. Such a transmitter may be assigned a unique PRN code so as to permit identification by a remote receiver. Pseudolites may be useful in situations where SPS signals from an orbiting satellite might be unavailable, such as in tunnels, mines, buildings, urban canyons or other enclosed areas. Another implementation of pseudolites is known as radio-beacons. The term "satellite", as used herein, is intended to include pseudolites, equivalents of pseudolites, and possibly others. The term "SPS signals", as used herein, is intended to include SPS-like signals from pseudolites or equivalents of pseudolites.

As used herein, mobile station (MS) refers to a device that may from time to time have a position or location that changes. The changes in position and/or location may comprise changes to direction, distance, orientation, etc., as a few examples. In particular examples, a mobile station may comprise a cellular telephone, wireless communication device, user equipment, laptop computer, personal navigation device (PND), personal multimedia player (PMP), other personal communication system (PCS) device, and/or other portable communication device. A mobile station may also comprise a processor and/or computing platform adapted to perform functions controlled by machine-readable instructions.

As discussed above, the utilization of multiple sensors to perform measurements may present a number of challenges to users of these devices. Such challenges may include, for example, size, cost, interfaces, connectivity, and/or power consumption of the multiple sensors. In order to address these issues, techniques described herein may include integrating two or more sensors in a single device. Such a device may comprise a component in a mobile station, for example.

Techniques described herein may implement a multi-sensor measurement processing unit (MSMPU) to support a wide range of applications such as those mentioned above, for example, although the scope of claimed subject matter is not limited to those particular applications. The MSMPU, in one aspect, may support these applications by providing desirable signal amplification, conditioning, measurement collection, measurement pre-processing, power management of internal and/or external components (including externally connected or accessible sensors), and/or communication of raw and/or pre-processed sensor data to an external processor. The external processor may comprise, for example, a mobile station (MS) modem or any other processor.

FIG. 1 is a block diagram of an example MSMPU 100 coupled to an MS modem (MSM) 110, which may comprise a processor. For this example, MSMPU 100 includes a pair of sensors, 130 and 140. Also included in this example is a local processor 120. Sensor 130 and/or sensor 140 may comprise any of a wide range of sensor types, including, but not limited to, accelerometers, gyroscopes, geomagnetic, pressure, biometric, and temperature sensors, etc. In one aspect, local processor 120 may comprise a power management system comprising, for example, circuitry and/or may execute a power management program. Sensors 130 and 140 may transition between power stages under control of the power management system in order to selectively control power consumption in one or both sensors. For example, sensor 130 may be placed in an "off" or "sleep mode" state where the sensor is drawing little or no power. Sensor 140 may operate in a low power mode, perhaps with limited functionality. Sensor 140 may at some point detect a trigger event. If sensor 140 detects a trigger event, local processor 120 may turn on sensor 130, and may also place sensor 140 in a normal operating mode. Alternatively, in another aspect, sensor 140 may operate in a normal mode while sensor 130 may be placed in an "off" or "low power mode" state. If sensor 140 detects a trigger event, local processor 120 may turn on sensor 130 and place it in a normal operating mode as well.

In one aspect, the power management system may comprise dedicated logic in local processor 120. Dedicated logic may manage power on/off, reduced power operation, and/or sleep modes for various internal and/or external components. For example, dedicated logic may provide power management for sensors 130 and 140. In another aspect, the power management system may be implemented at least in part as software instructions that are executable on local processor 120.

Figure 2:
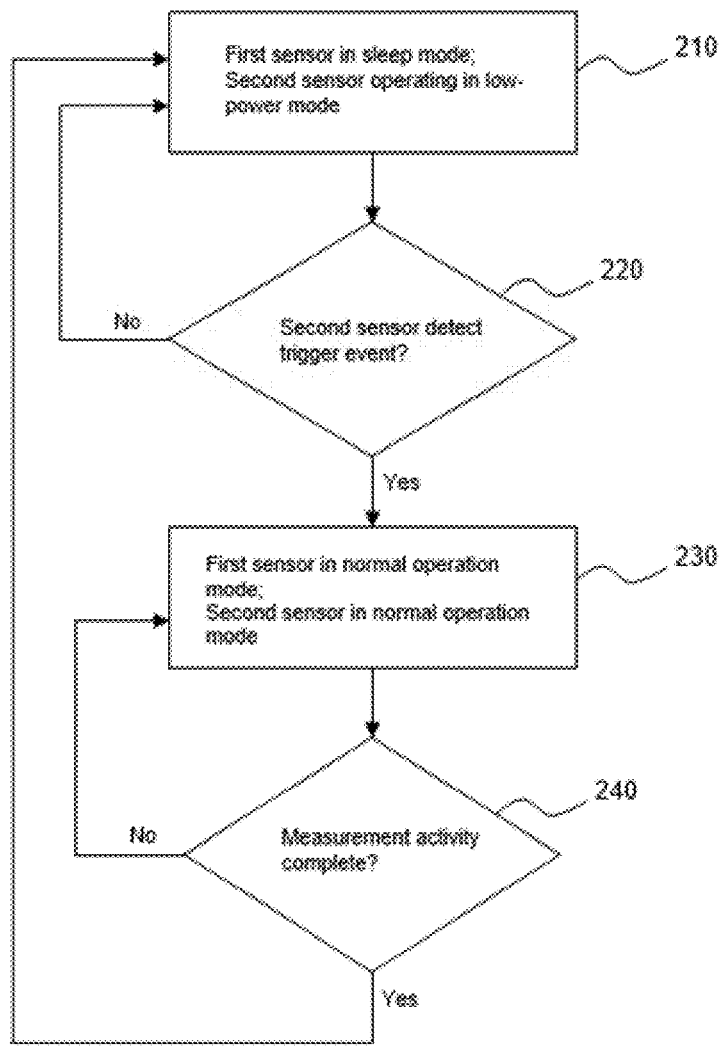
FIG. 2 is a flow diagram of an example process for power managing a plurality of sensors integrated within a single device.

FIG. 2 is a flow diagram of an example process for power managing a pair of sensors situated within a mobile station. At block 210, a first sensor is in a sleep mode or "off" mode, meaning that the first sensor is drawing little or no power. Also at block 210, a second sensor is operating in a low-power mode. At block 220, a determination may be made as to whether the second sensor has detected a trigger event. In response to the second sensor detecting a trigger event, at block 230 the first sensor may be placed into a normal operational mode and the second sensor may also be placed into a normal operational mode in order to perform a measurement activity. The two sensors may stay in the normal operational modes until the measurement activity is completed. At block 240, if the measurement activity is completed, the first sensor may be turned off or put in a "sleep" mode while the second sensor is placed into the low-power mode at block 210. Examples in accordance with claimed subject matter may include all, more than all, or less than all of blocks 210-240. Further, the flow diagram of FIG. 2 is merely an example technique for power managing a pair of sensors, and claimed subject matter is not limited in this respect.

Figure 3:
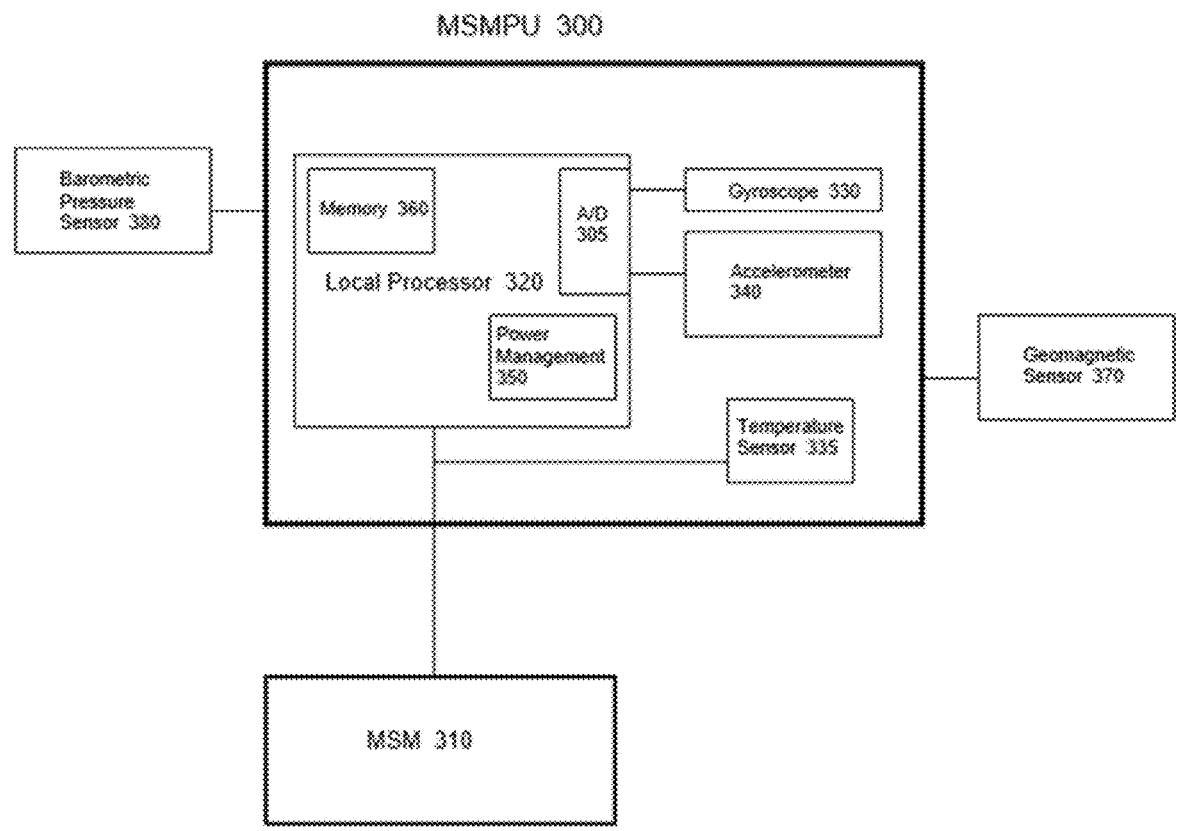
FIG. 3 is a block diagram of an additional example of a multi-sensor measurement processing unit.

FIG. 3 is a block diagram of an example MSMPU 300 comprising a local processor 320, a memory 360, a power management unit 350, a gyroscope 330, and accelerometer 340, and a temperature sensor 335. MSMPU 300 may be coupled to an external processor, such as, for example, MSM 310. For this example, gyroscope 330 and/or accelerometer 340 may provide analog signals to local processor 320. MSMPU may comprise an analog-to-digital converter (A/D) 305 for digitizing analog signals from gyroscope 330, accelerometer 340, and/or other sensors. For this example, a geomagnetic sensor 370 and a barometric pressure sensor 380 are coupled to MSMPU 300. In one aspect, signal amplification and conditioning circuitry may be included to process externally connected analog sensors such as geomagnetic sensor 370. Although example MSMPU 300 is described with A/D 305 and memory 360 as being integrated within local processor 320, other examples are possible with one or both of A/D 305 and memory 360 not integrated within local processor 320. Further, the particular arrangement and configuration of MSMPU 300 is merely an example, and the scope of claimed subject matter is not limited in these respects.

For this example, geomagnetic sensor 370 is not integrated into MSMPU 300, but is disposed elsewhere within the device incorporating MSMPU 300. The ability to position the geomagnetic sensor separately from MSMPU may allow for flexible placement of the geomagnetic sensor.

Accordingly, such flexibility in placement of a geomagnetic sensor may enable greater flexibility in form factor design and placement to reduce the effects of electromagnetic interference and/or temperature, for example.

In one aspect, external sensors 370 and/or 380 as well as MSM 310 may be coupled to MSMPU 300 via any of a wide range of interconnect types, including, but not limited to, I2C and/or SPI interconnects. Of course, this is merely an example interconnect type, and the scope of claimed subject matter is not limited in this respect.

In another aspect, MSMPU 300 may implement an interrupt pin coupled to MSM 310 or another component. MSMPU 300 may operate the interrupt signal in a latched interrupt mode, for one example. Further, MSMPU 300 may incorporate an internal programmable threshold and dedicated circuitry to set the interrupt pin. However, these are merely examples of how interrupt signaling may be implemented, and the scope of claimed subject matter is not limited in this respect.

In another aspect, MSMPU 300 may implement at least one general programmable IO pin (GPIO) coupled to MSM 310 or another component. MSMPU 300 may operate the GPIO pin to power on and off a connected component, for one example.

In another aspect, power management unit 350 may provide power control signals to gyroscope 330 and accelerometer 340. Power management unit 350 may be implemented as dedicated circuitry, or may be implemented as software and/or firmware stored in memory 360 and executed by local processor 320.

For one example, gyroscope 330 may be turned off while accelerometer 340 is operating in a low power mode. Accelerometer 340 may operate while in the low power mode to detect motion of the device incorporating the MSMPU 300. If motion is detected, accelerometer 340 may be put into a normal operational mode and gyroscope 330 may also be powered on and put into a normal operational mode. In one aspect, each of the sensors 330 and 340, as well as for some implementations external sensors such as geomagnetic sensor 370 and barometric sensor 380, may be powered on, put to sleep, put into low power operational modes, and/or put into normal operational modes independently of one another. In this manner, power management unit 350 may tailor power consumption across a wide range of possible applications, situations, and performance requirements. In another aspect, MSMPU 300 may implement a fast procedure to restore power for gyroscope 330 and/or accelerometer 340. In one example, one of two or more fast procedures to restore power (wake up modes) may be selected, wherein the different modes represent various compromises between wake up time and current consumption.

For an example, the output of accelerometer 340 may be used as a switch to turn on other sensors integrated within MSMPU 300 or elsewhere within the device incorporating MSMPU 300. Such external sensors may be incorporated on the same die as MSMPU 300 or may be implemented as a single system-in-package (SIP). External sensors may also be situated outside of the device incorporating MSMPU 300, perhaps remotely connected with MSMPU 300 via a wireless interconnect, as described further below, or via another type of interconnect.

In another aspect, sensors integrated within MSMPU 300 may have programmable and/or selectable characteristics. For example, accelerometer 340 may implement a selectable "g" level, perhaps with a range of from 2 to 16 g, in one example. For another example, gyroscope 330 may have a selectable angular velocity range, perhaps ranging from 50 to 500 deg/sec for one example. However, these are merely example ranges for accelerometer 340 and gyroscope 330, and the scope of claimed subject matter is not limited in these respects.

In a further aspect, MSMPU 300 may incorporate a selectable output resolution for measurement data. In one example, resolutions of either seven bits for low power consumption modes or fourteen to sixteen bits for normal operational modes may be selected. Also, MSMPU may operate at a selectable bandwidth for the interface to MSM 310. For one example, the bandwidth may be selectable between 25 and 1500 Hz.

In another aspect, MSMPU 300 and its associated sensors may be used in navigational applications. Accelerometer 340 may be pre-programmed and/or preconfigured to detect the movement (change in acceleration) and/or change in the tilt angle of the device incorporating MSMPU 300 as either exceeding, falling below, or being between two thresholds (upper and lower) to trigger power management functions for one or more of the other sensors. In this manner, for this example, geomagnetic sensor 370 and/or gyroscope 330 and/or barometric pressure sensor 380 and/or a camera sensor (not shown) and/or any other sensor integrated into the device incorporating the MSMPU or remotely connected to the MSMPU can be powered on if motion is detected in order to perform the navigation application. Similarly, if motion is not detected (the device is stationary), the accelerometer output may be used to put any or all the other sensors in a sleep, low power, or off mode, thus reducing the power consumption.

Figure 4:
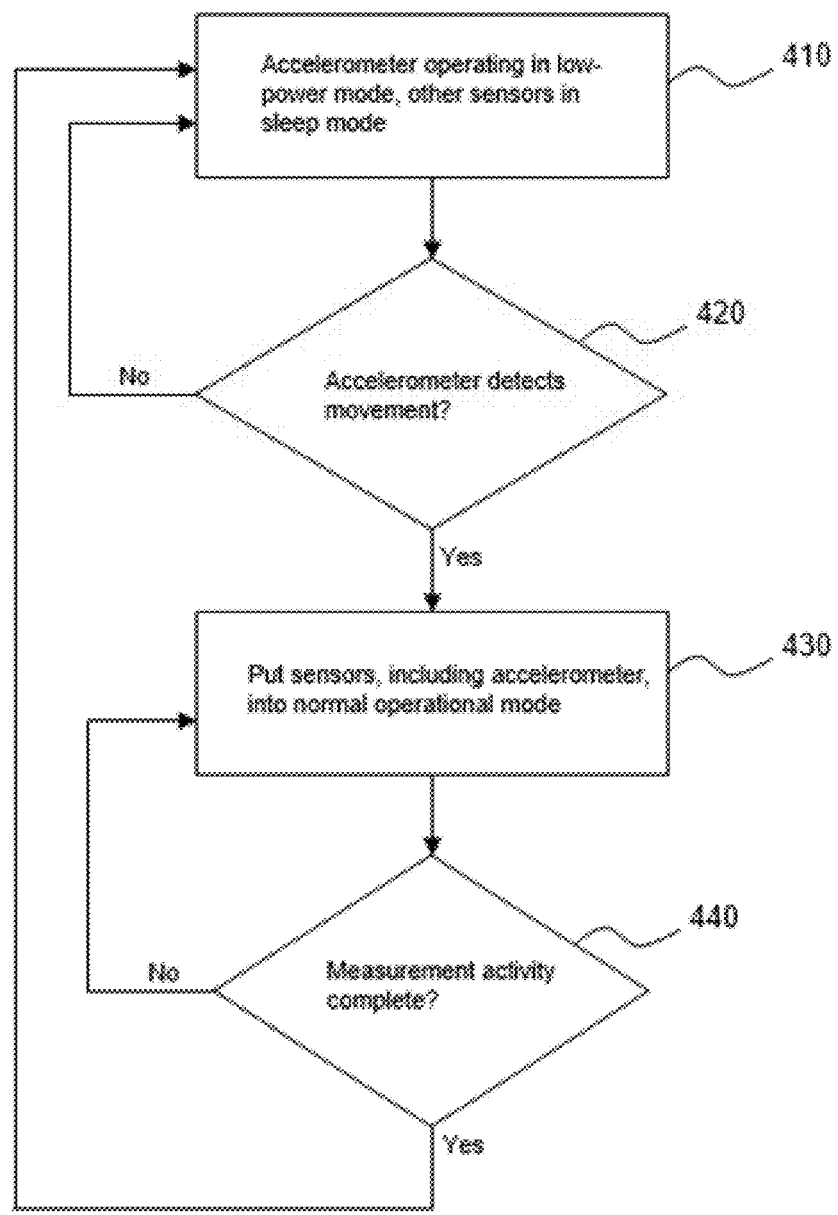
FIG. 4 is a flow diagram of an example process for switching operational modes of a gyroscope in response to motion detected by an accelerometer.

FIG. 4 is a flow diagram of an example process for power managing two or more sensors including an accelerometer within a mobile station. At block 410, one or more sensors are in a sleep mode, meaning that the one or more sensors are drawing little or no power. Also at block 410, an accelerometer may operate in a low-power mode. Block 420 indicates that if the accelerometer detects movement, at block 430 the one or more sensors previously put in sleep mode may be wakened to operate in a normal operational mode. The accelerometer may also be put into a normal operational mode in order to perform a measurement activity in conjunction with the one or more other sensors, perhaps including a gyroscope and/or a geomagnetic sensor. The various sensors may stay in the normal operational modes until the measurement activity, perhaps including navigational operations for one example, is completed. At block 440, if the measurement activity is completed, the one or more sensors may be returned to sleep mode and the accelerometer may be placed into the low-power mode at block 410. Examples in accordance with claimed subject matter may include all, more than all, or less than all of blocks 410-440. Further, the flow diagram of FIG. 4 is merely an example technique, and claimed subject matter is not limited in this respect.

In another aspect, accelerometer 340 may be used to detect a free-fall condition of the device incorporating the MSMPU, perhaps a mobile station, in order to power down gyroscope 330 to protect the gyroscope from damage upon impact. This process may be analogous to a process of parking a read/write head of a hard disk to protect it from impact of a fall.

As previously described, the power control logic implemented within MSMPU 300 may power on or off or switch the operational modes of not only the internal sensors such as accelerometer 340 and gyroscope 330, but may also power on or off or switch the operational modes of external sensors such as geomagnetic sensor 370 and barometric pressure sensor 380. In another aspect, power management unit 350 may also be adapted to power on or off or switch the operational modes of an external processor, such as, for one example, MSM 310. In a further aspect, power management unit 350 may execute processes to determine conditions under which it may be advantageous to switch modes of operation for various internal and external sensors and/or processors and/or other components. Of course, these are merely examples of power management processes that may be executed by power management unit 350, and the scope of claimed subject matter is not limited in this respect.

In another example, local processor 320 may be used to detect motion based on the measurements from at least one of accelerometer 340 and gyroscope 330. Furthermore, the motion detection event may be used to start the execution of the instructions resident on an external processor such as MSM 310.

Figure 5:
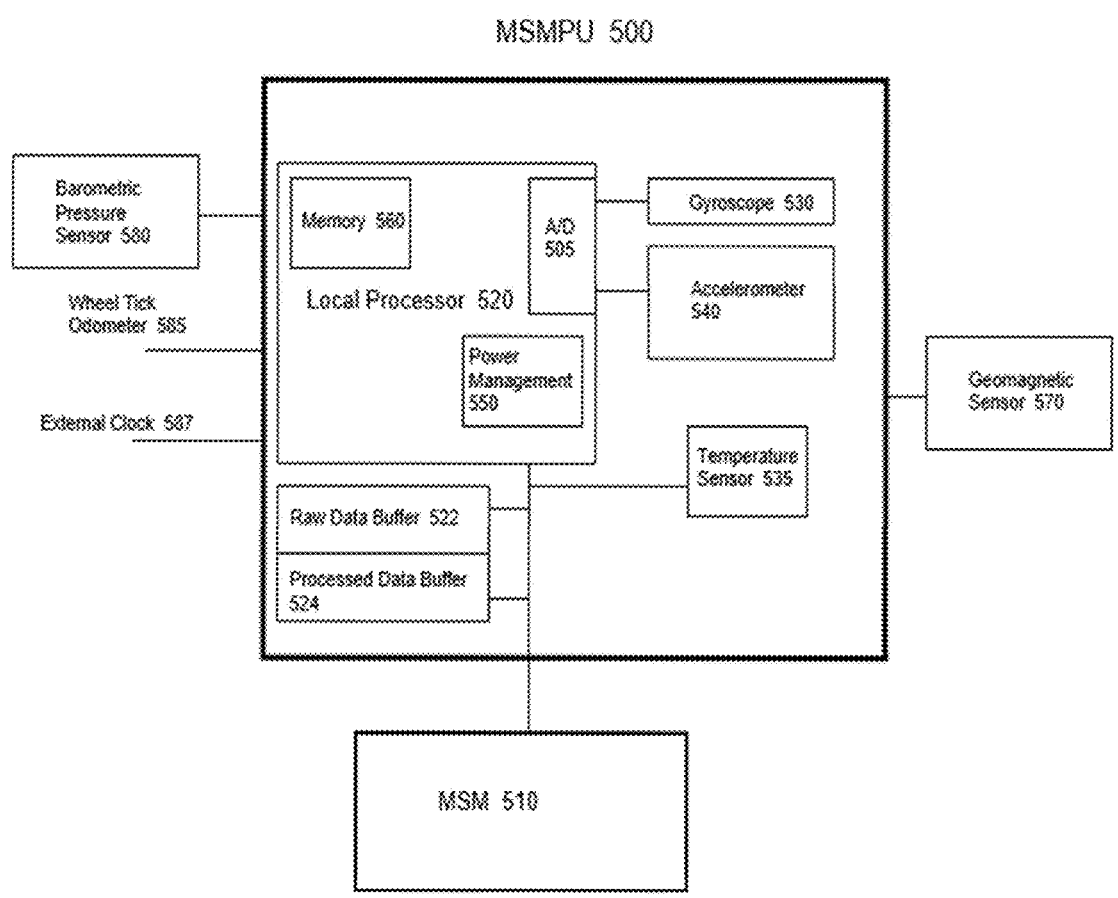
FIG. 5 is a block diagram of a further example of a multi-sensor measurement processing unit.

FIG. 5 is a block diagram of an example MSMPU 500 coupled to a mobile station modem (MSM) 510. MSMPU 500 and MSM 510 may, for one example, be incorporated into a mobile station. MSMPU 500 may comprise a local processor 520, a memory 560, a power management unit 550, a gyroscope 530, an accelerometer 540, and a temperature sensor 535. For one example, gyroscope 530 and/or accelerometer 540 may provide analog signals to local processor 520. MSMPU may comprise an analog-to-digital converter (A/D) 505 for converting analog signals from gyroscope 530, accelerometer 540, and/or other sensors. In an aspect, power management unit 550 may provide power control signals to gyroscope 530 and accelerometer 540. Power management unit 550 may be implemented as dedicated circuitry, or may be implemented as software and/or firmware stored in memory 560 and executed by local processor 520. For this example, MSMPU 500 may further be coupled to a barometric pressure sensor 580 and a geomagnetic sensor 570, and may also receive a wheel tick/odometer signal 585 and an external clock signal 587. However, this is merely one example configuration of an MSMPU and associated sensors and signals, and the scope of claimed subject matter is not limited in this respect.

Also for this example, MSMPU may comprise one or more buffers adapted to store data from sensors, and/or from local processor 520, and/or from an external processor such as MSM 510. For the example depicted in FIG. 5, MSMPU 500 may comprise a raw data buffer 522 and a processed data buffer 524. The buffering capability provided by buffers 522 and/or 524 may be used for various measurements being generated by various components included in and/or coupled to MSMPU 500. For example, a rate at which measurements may be obtained from one or more sensors may be different from a rate at which these measurements are either processed in by the local processor 520 and/or transmitted to an external component such as an external processor, perhaps MSM 510 in one example. Further, measurement data from one or more sensors may be collected in one or more buffer in order to transmit the data to MSM 510 or other component in a burst fashion. In another aspect, raw data buffer 522 may be used to store data in its raw form (as delivered by one or more sensors) and the processed data buffer may be used for data that may have been processed in some fashion either by local processor 520 or by an external processor such as MSM 510. Such processing may include any type of filtering, averaging, sub-sampling, outlier detection, and/or time stamping the data to associate an instance of time with one or more measurements. Of course, the buffering techniques described herein are merely example techniques, and the scope of claimed subject matter is not limited in this respect.

Yet another aspect may comprise the time stamping of various sensor measurements upon storing the measurements in a buffer, such as, for example, either buffer 522 or buffer 524, or upon storing the measurements in a memory, such as, for example, memory 560. Measurement data may also be time-stamped upon transmitting the measurement data to an external component, such as, for example, MSM 510. The time stamping may be based, in an example, upon a clock signal received over external clock signal 587. For an example, external clock signal 587 may be generated by any of various common crystals, for example a 32 KHz crystal. The external clock signal may also be used by local phase-locked loop (PLL) circuitry to synthesize the higher frequency signal needed to run the local processor.

In another aspect, a periodic time reference pulse, perhaps one pulse per second for one example, may be accepted by MSMSPU 500 from MSM 510 or other external processor which has access to a reference time standard such as that provided by an SPS, or by the Coordinated Universal Time (UTC) standard, or by any other well known system time. Buffer data may be time-stamped with information derived from such system time information, for example time information derived from an SPS. In this manner, time stamps may be synchronized to a reference time that may enable a combination of sensor data with other time-stamped data, such as SPS satellite measurements for navigation applications. In another aspect, an external processor (for example, a client for sensor information) may provide timing information such as start and stop times to define a measurement period for the sensor data. In a navigation application these start and stop times may correspond to sequential SPS measurement time tags and may be used to synchronize the sensor data to the received SPS data. Using SPS time tags to define a measurement period is merely one example technique, and time tags from a number of different sources may be used to define measurement time periods in other examples.

Figure 6:
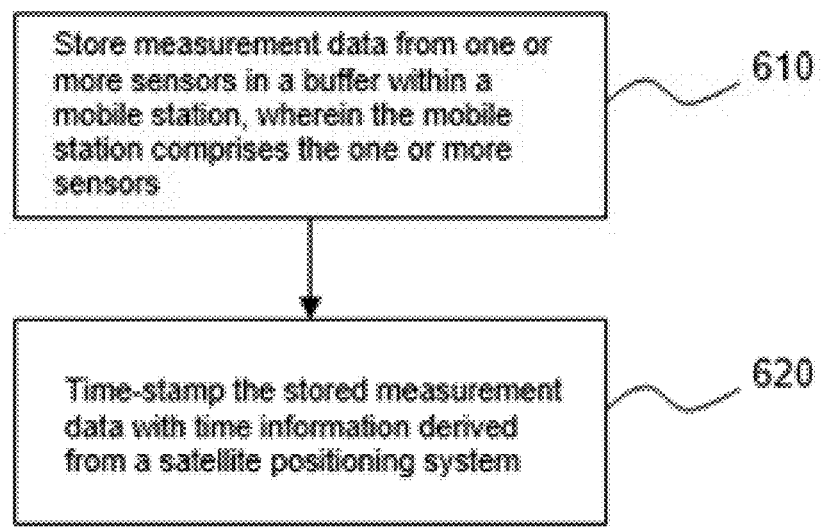
FIG. 6 is a flow diagram of an example process for time-stamping buffered sensor data.

FIG. 6 is a flow diagram of an example process for time-stamping measurement data. At block 610, measurement data from one or more sensors may be stored in a buffer within a mobile station, wherein the mobile station comprises the one or more sensors. At block 620, the stored measurement data may be time-stamped with time information derived from a satellite positioning system or any other common reference system. Examples in accordance with claimed subject matter may include all, more than all, or less than all of blocks 610-620. Further, the flow diagram of FIG. 6 merely illustrates an example technique, and claimed subject matter is not limited in this respect.

In another aspect, a periodic time reference pulse signal such as that received via external clock 587 or via an SPS or other time pulse source may be used to initiate a transmission of sensor data from buffers 522 and/or 524 or from memory 560 to an external component such as MSM 510. For example, MSMPU 500 may process sensor measurements according to desired processes, store the sensor data either in one or both of buffers 522 and 524 or in memory 560, and then transmit the sensor data in response to receiving the periodic time reference signal or in response to receiving a "ready to receive" message from an external component, such as, for example, MSM 510 or from a device in communication with MSM 510.

In another example, initiation to transmit may be triggered by a receipt of a "ready to receive" message over any common I/O peripheral or interface such as I2C, SPI, UART, parallel port, etc. Same peripherals and/or interfaces may be used to provide the external timing information to MSMPU 500 for measurement time stamping and/or maintenance of the synchronization between MSMPU 500 and external component such as MSM 510.

In another aspect, circuitry and/or software may be provided to calibrate sensors either integrated within MSMPU 500 and/or externally connected to MSMPU 500. If an external processor such as MSM 510 is used to execute a navigation application, the navigation application may estimate one or more states associated with an object such as a mobile station. The one or more states may include, but are not limited to, geographic location, altitude, speed, heading, orientation, and/or the like. The one or more estimated states may provide information that may be used to calibrate various parameters of sensors incorporated within the mobile station. Examples of such parameters may include accelerometer bias, drift, bias as a function of temperature, drift as a function of temperature, measurement noise as a function of temperature, sensitivity as a function of temperature, variation in any of the parameters as a result sensor installation (mounting) on the board or aging, etc. However, these are merely examples of parameters that may be calibrated, and the scope of claimed subject matter is not limited in this respect.

Figure 7:
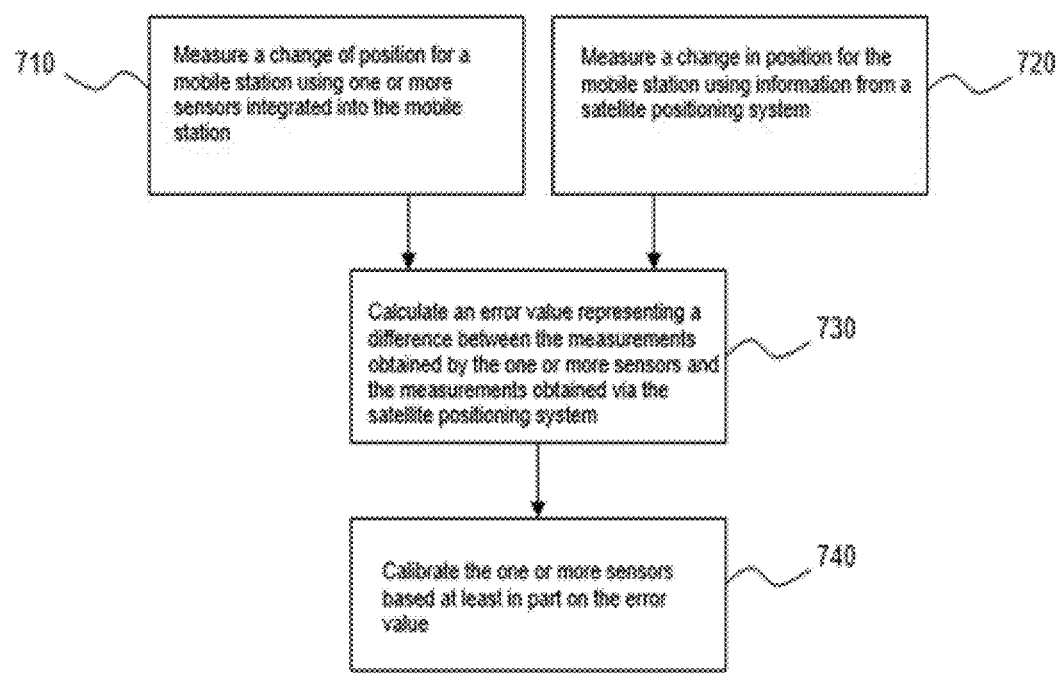
FIG. 7 is a flow diagram of an example process for calibrating sensors.

FIG. 7 is a flow diagram of an example process for calibrating a sensor. At 710, a change in at least one of position, velocity and altitude for a mobile station may be measured using one or more sensors integrated into the mobile station. The change in position may be measured, for an example, measuring a direction and/or distance traveled for the mobile station. A change in position for the mobile station may be measured using information from a satellite positioning system at 720. At 730, an error value may be calculated wherein the error value represents a difference between the measurements obtained by the one or more sensors and the measurements obtained via the satellite positioning system. At 740, the one or more sensors may be calibrated based at least in part on the error value. Examples in accordance with claimed subject matter may include all, more than all, or less than all of blocks 710-740. Further, the flow diagram of FIG. 7 merely illustrates an example technique for calibrating a sensor, and claimed subject matter is not limited in this respect.

In another aspect, circuitry and/or software and/or firmware may be provided to allow a determination that the device incorporating MSMPU 500 is stationary. The determination may be performed by software and/or firmware executed on local processor 520 or may be provided via an external input. For example, a wheel tick/odometer input signal 585 may indicate a stationary condition. In one aspect, wheel tick/odometer input signal 585 may be used in performing sensor calibration processes. In another aspect, the stationary condition may be used to calibrate gyroscope 530 and/or barometric pressure sensor 580. If the device incorporating MSMPU 500 is known to be stationary, any change in pressure can be attributed to the actual variation in pressure and not to a change in altitude.

In a further aspect, MSMPU may be incorporated into any of a range of devices, including, for example, cell phones, personal digital assistants, notebook computers, etc. Such devices may on occasion be placed into a cradle or docking station. In one example, when such a device is placed in the cradle or docking station, the device is stationary. MSMPU 500 may sense or may receive an indication that such a device is placed in the cradle or docking station, deducing that the device is stationary. In an example, the indication of a stationary condition may be utilized in performing calibration operations such as discussed above. In another aspect, MSMPU 500 may detect the transition out of a stationary condition, for example through motion detection.

In an additional aspect, temperature sensor 535 may provide temperature measurements that may be used in performing calibration operations in order to develop sensor performance characteristics as a function of temperature. In one example, a table of accelerometer drift values as a function of temperature may be learned and stored in memory 560. The sensor calibration data (such as bias and drift) may be provided to MSMPU 500 for sensor data correction. Correcting raw sensor data with calibration data may provide capabilities for various applications, including, but not limited to, motion detection and motion integration for dead-reckoning application. Dead reckoning (DR) may refer to a process of estimating one's current position and advancing that position based on known or measured speed, elapsed time, and heading.

In another aspect, data from geometric sensor 570 may be used to calibrate gyroscope 530 biases and may also be used to initialize an absolute heading indicated by the geomagnetic sensor. In order to provide better directional information, it may be advantageous for geomagnetic sensor 570 to be tilt-compensated using roll and pitch measurements from accelerometer 540. Tilt-compensation processes may be implemented by dedicated circuitry resident on MSMPU 500 and/or may be implemented in software and/or firmware that may be executed by local processor 520 and/or MSMPU 500. The tilt-compensation processes may utilize measurement data received from externally connected geomagnetic sensor 570. It may also be advantageous to incorporate data from temperature sensor 535 or from another temperature sensor either integrated into geomagnetic sensor 570 or placed in close proximity to geomagnetic sensor 570. In another aspect, gyroscope 530 may be calibrated using sequential and/or periodic and/or event-triggered measurements from geomagnetic sensor 570 to measure the change in the angular information.

In yet another aspect, MSMPU 500 may perform motion integration by incorporating measurements from accelerometer 540 and gyroscope 530 to determine the change in the distance and direction traveled (e.g., trajectory or path of motion). This aspect may be advantageously employed in geo-fencing applications where it is desirable to determine if an object incorporating MSMPU 500 has exited or entered an area of interest. The area of interest may be defined as a circle with a preset and/or programmable radius, for an example, although this is merely an example of how an area of interest may be defined, and the scope of claimed subject matter is not limited in this respect.

Figure 8:
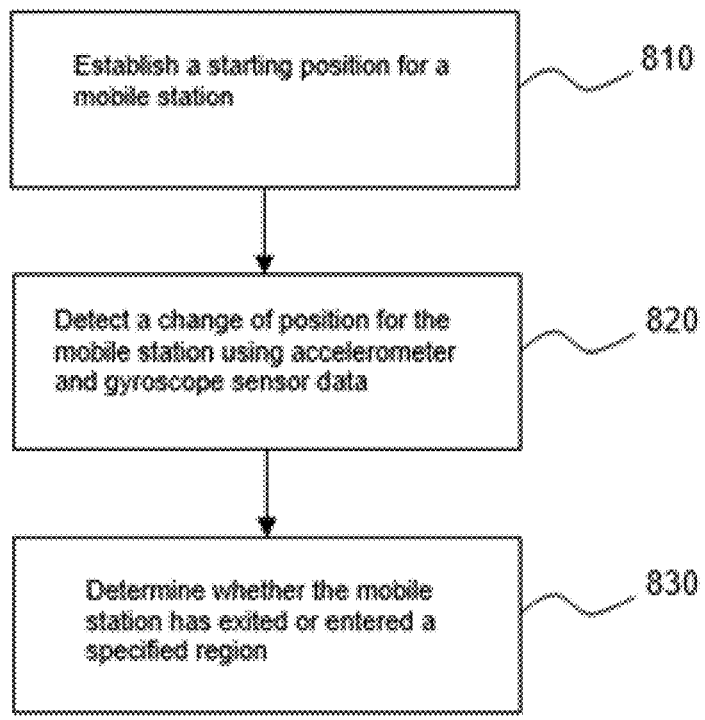
FIG. 8 is a flow diagram of an example process for determining whether a mobile station has entered or exited a specified region.

FIG. 8 is a flow diagram illustrating an example geo-fence application. At block 810, a starting position may be established for a mobile station. At block 820, a change in position for the mobile station may be detected using accelerometer and gyroscope sensor data. The change in position may be detected, in an example, by detecting a direction and/or distance traveled for the mobile station using techniques known to those of ordinary skill in the art. At block 830, a determination may be made as to whether the mobile station has exited or entered a specified region. Examples in accordance with claimed subject matter may include all, more than all, or less than all of blocks 810-830. Further, the flow diagram of FIG. 8 merely illustrates an example technique for geo-fencing, and claimed subject matter is not limited in this respect.

Figure 9:
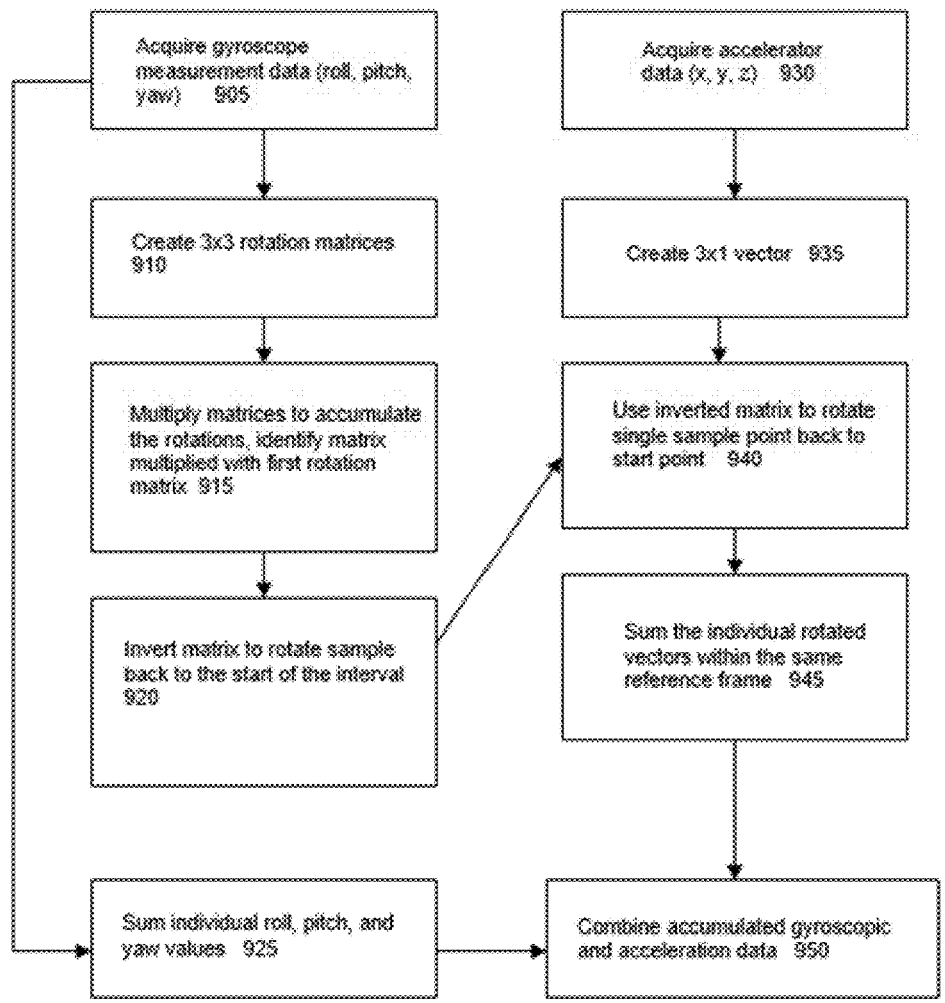
FIG. 9 is a flow diagram of an example process for combining accelerator and gyroscope measurements.

FIG. 9 is a flow diagram of an example process for combining information from both accelerometer 540 and gyroscope 530. Such information may comprise motion integration and rotation data, and such information may be utilized to support geo-fencing and/or navigation DR operations. In general, information from gyroscope 530 may be used to compute how much the mobile station's orientation has been rotated from the original orientation, in three dimensional space. The resulting rotation matrix may be used to convert the accelerometer information back to the measurement frame (orientation) that the accelerometer was in at the beginning of the measurement period. These "rotated" measurements may be added to previous measurements to determine a net displacement, because the measurements are all based on the same orientation. In particular, for this example technique, at block 905, data may be acquired from a gyroscope, such as, for example gyroscope 530. At block 910, 3×3 matrices may be created, and at block 925 individual roll, pitch, and yaw (heading) values may be summed. The matrices from block 910 may be multiplied at block 915 to accumulate the rotations. A matrix multiplied with the first rotation matrix may be identified. At block 920, the matrix may be inverted to rotate the sample back to the start of the interval. Processing may proceed to block 940. At block 930, accelerometer data (x, y, z) may be acquired, and at block 935 a 3×1 vector may be created. At block 940, the inverted matrix from block 920 may be used to rotate the sample point back to the starting point. At block 945, individual frames from within the same reference frame may be summed. At block 950, the accumulated rotations (from gyroscope measurements) and distance traveled (from accelerometer measurements) may be combined. Examples in accordance with claimed subject matter may include all, more than all, or less than all of blocks 905-950. Further, the flow diagram of FIG. 9 merely illustrates an example technique for combining accelerator and gyroscope measurements, and claimed subject matter is not limited in this respect.

Figure 10:
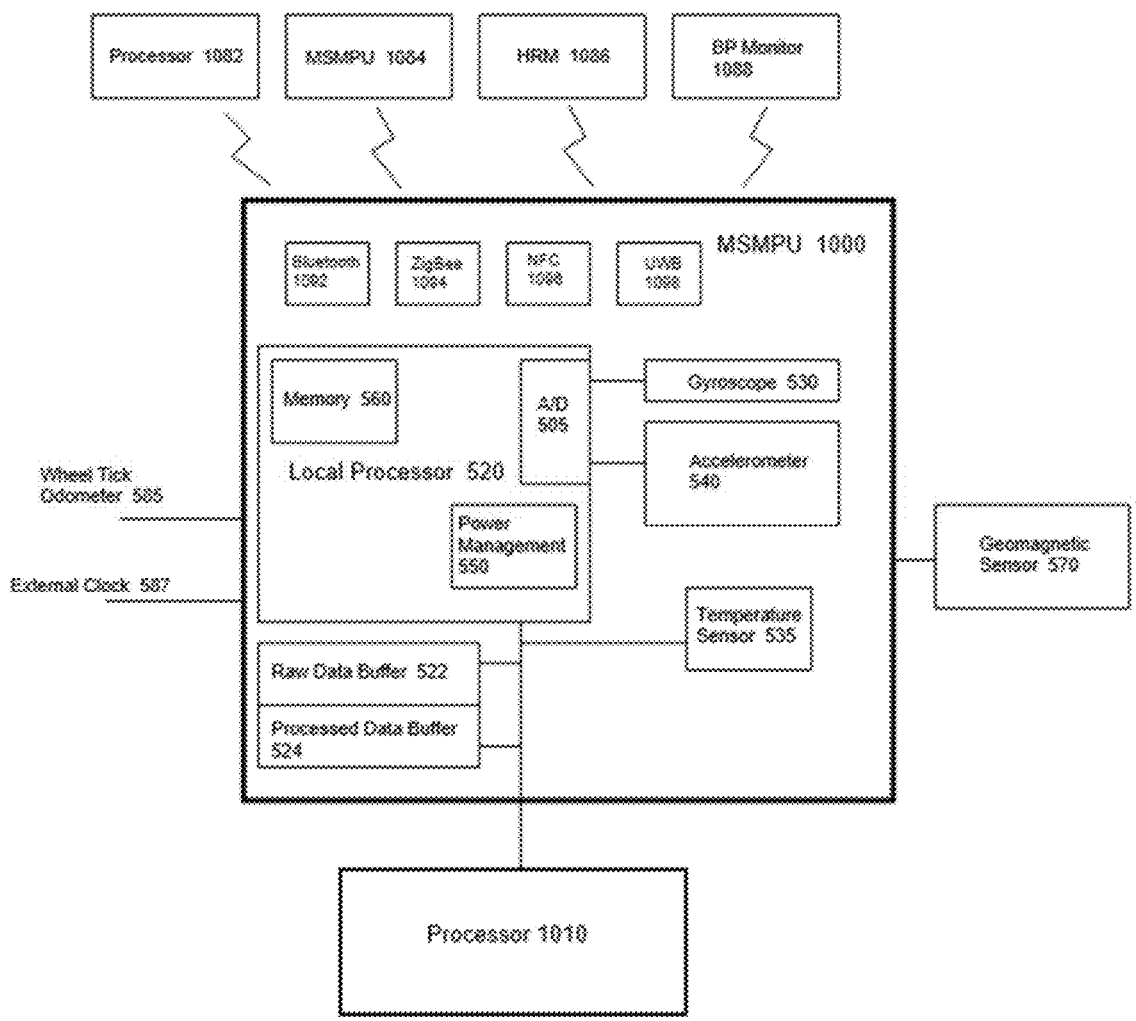
FIG. 10 is a block diagram of an additional example of an MSMPU.

FIG. 10 is a block diagram of an example MSMPU 1000 comprising wireless connectivity. MSMPU may comprise similar technologies as described above in connection with FIGS. 3 and 5. Wireless connectivity may be accomplished via any of a wide range of wireless technologies, including future technologies. Bluetooth, ZigBee, Near Field Communication (NFC), WiFi, and Ultra Wide Band (UWB) are just a few examples of such wireless technologies, and the scope of claimed subject matter is not limited in this respect. These technologies are represented in FIG. 10 by wireless communication units 1092, 1094, 1096, and 1098. By adding wireless connectivity, a device integrating MSMPU 1000 may be able to communicate with another device which also includes an MSMPU 1084 for peer-to-peer applications such as multi-player games, as one example. MSMPU 1000 may also communicate with an external processor 1082 to provide processor 1082 with raw sensor measurements, processed sensor measurements, positional (x,y,z) and/or attitude information (τ,φ,ψ) in any number of degrees (depending on the availability and operational status of integrated or connected sensors), change in positional and/or attitude information, Euler angles, quaternion, telemetry data, etc.

In another aspect, MSMPU 1000 may also communicate through any of the wireless technologies with one or more biometric sensors, such as, for example, heart rate monitor (HRM) 1086 and/or blood pressure (BP) monitor 1088. Such sensors may find application in medical and/or fitness/athletic fields, for example.

Information gathered from internal and/or external sensors may be used by external processor 1082 to derive a navigational solution, and/or user interface and/or gaming control signals, camera image stabilization signals, etc. In another example, data from at least one MSMPU may be provided to a central processing unit to derive a relative positional and/or attitude information that may be used in a multi-player gaming environment where actions or change in position or change in attitude of one player with respect to another player are desirable to know.

Figure 11:
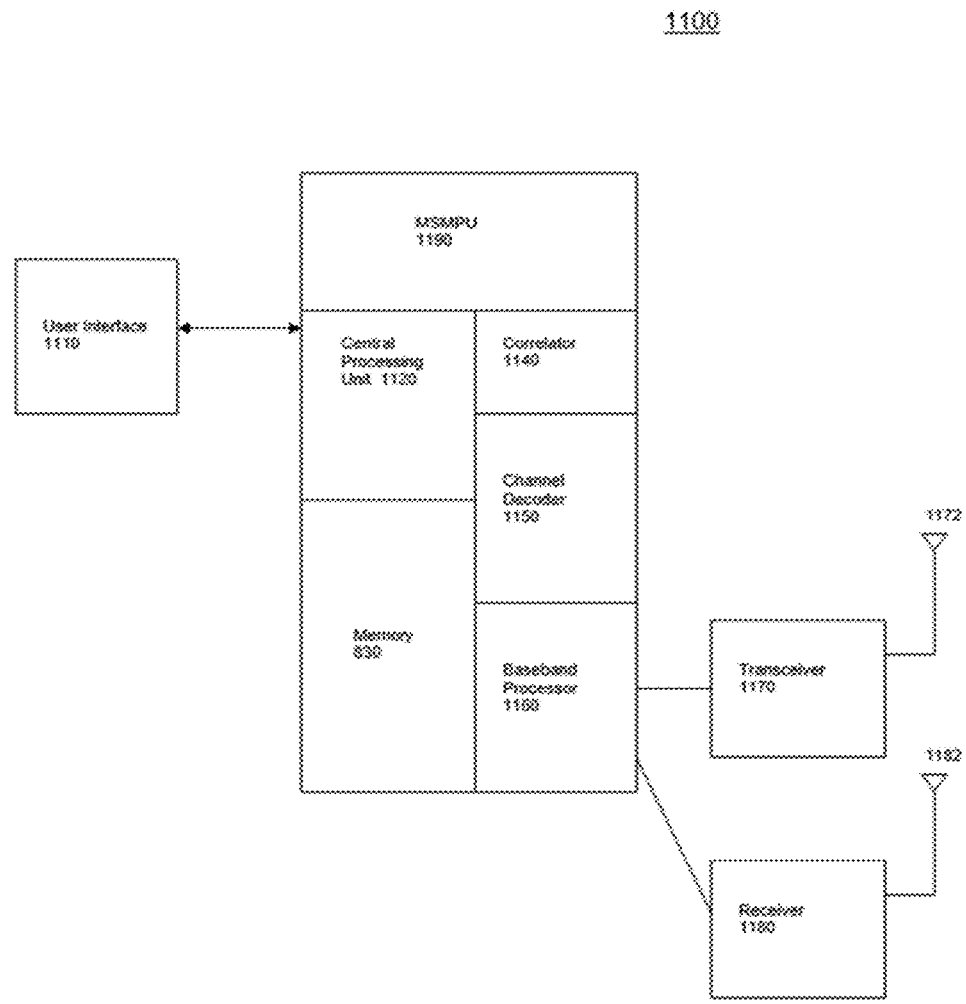
FIG. 11 is a block diagram of an example mobile station incorporating an MSMPU.

FIG. 11 is a block diagram of an example of a mobile station 1100. A radio transceiver 1170 may be adapted to modulate an RF carrier signal with baseband information, such as voice or data, onto an RF carrier, and demodulate a modulated RF carrier to obtain such baseband information. An antenna 1172 may be adapted to transmit a modulated RF carrier over a wireless communications link and receive a modulated RF carrier over a wireless communications link.

A baseband processor 1160 may be adapted to provide baseband information from a central processing unit (CPU) 1120 to transceiver 1170 for transmission over a wireless communications link. Here, CPU 1120 may obtain such baseband information from an input device within a user interface 1110. Baseband processor 1160 may also be adapted to provide baseband information from transceiver 1170 to CPU 1120 for transmission through an output device within user interface 1110.

User interface 1110 may comprise a plurality of devices for inputting or outputting user information such as voice or data. Such devices may include, by way of non-limiting examples, a keyboard, a display screen, a microphone, and a speaker.

A receiver 1180 may be adapted to receive and demodulate transmissions from an SPS, and provide demodulated information to correlator 1140. Correlator 1140 may be adapted to derive correlation functions from the information provided by receiver 1180. Correlator 1140 may also be adapted to derive pilot-related correlation functions from information relating to pilot signals provided by transceiver 1170. This information may be used by a mobile station to acquire wireless communications services. Channel decoder 1150 may be adapted to decode channel symbols received from baseband processor 1160 into underlying source bits. In one example where channel symbols comprise convolutionally encoded symbols, such a channel decoder may comprise a Viterbi decoder. In a second example, where channel symbols comprise serial or parallel concatenations of convolutional codes, channel decoder 1150 may comprise a turbo decoder.

A memory 1130 may be adapted to store machine-readable instructions which are executable to perform one or more of processes, implementations, or examples thereof which are described or suggested herein. CPU 1120 may be adapted to access and execute such machine-readable instructions.

Mobile station 1100 for this example comprises an MSMPU 1190. MSMPU 1190 may be adapted to perform any or all of the sensor measurement and/or power management operations described herein. For example, MSMPU 1190 may be adapted to perform the functions described above in connection with FIGS. 1-10.

While there has been illustrated and described what are presently considered to be example features, it will be understood by those skilled in the art that various other modifications may be made, and equivalents may be substituted, without departing from claimed subject matter. Additionally, many modifications may be made to adapt a particular situation to the teachings of claimed subject matter without departing from the central concept described herein. Therefore, it is intended that claimed subject matter not be limited to the particular examples disclosed, but that such claimed subject matter may also include all aspects falling within the scope of the appended claims, and equivalents thereof.

The invention claimed is:

1. A multi-sensor measurement processing unit, comprising:
   a processor;
   one or more sensors coupled to the processor; and
   a wireless interface unit coupled to the processor, wherein the wireless interface unit is adapted to receive, via an antenna, measurement information comprising satellite positioning system (SPS) measurements from an external sensor of a mobile station via a wireless interconnect and wherein the processor is further adapted to estimate one or more navigational states of the multi-sensor measurement processing unit based on the measurement information and data from an accelerometer and a gyroscope disposed within a device incorporating the multi-sensor processing unit, wherein the accelerometer data comprise x-axis, y-axis, and z-axis data, wherein the gyroscope data comprise roll, pitch, and yaw data, wherein the gyroscope data is used to determine how much the multi-sensor measurement processor unit has rotated relative to a previous orientation to determine rotated measurements, wherein the rotated measurements are combined to determine a net displacement, wherein the navigational states comprise at least one of a geographic location, altitude, speed, heading, or orientation; wherein the wireless interface unit is further adapted to change a power state of the accelerometer or gyroscope on the basis of a trigger event, wherein the trigger event is a change in navigational state.

2. The multi-sensor measurement processing unit of claim 1, wherein the wireless interface unit is adapted to receive measurement information from an external biomedical sensor.

3. The multi-sensor measurement processing unit of claim 2, wherein the biomedical sensor comprises a heart rate monitor.

4. The multi-sensor measurement processing unit of claim 2, wherein the biomedical sensor comprises a blood pressure monitor.

5. The multi-sensor measurement processing unit of claim 1, wherein the wireless interconnect comprises an interconnect implemented substantially according to a wireless standard.

6. The multi-sensor measurement processing unit of claim 1, wherein the wireless interconnect comprises an interconnect implemented substantially according to a near field communication standard.

7. The multi-sensor measurement processing unit of claim 1, wherein the wireless interface unit is adapted to receive measurement information from an external processor.

8. A method comprising:
   receiving, by a wireless interface unit of a multi-sensor measurement processing unit comprising one or more sensors, via an antenna, measurement information comprising satellite positioning system (SPS) measurements from an external sensor of a mobile station via a wireless interconnect;
   estimating one or more navigational states of the multi-sensor measurement processing unit based on the measurement information and data from an accelerometer and a gyroscope disposed within a device incorporating the multi-sensor processing unit, wherein the accelerometer data comprise x-axis, y-axis, and z-axis data, wherein the gyroscope data comprise roll, pitch, and yaw data, wherein the gyroscope data is used to determine how much the multi-sensor measurement processor unit has rotated relative to a previous orientation to determine rotated measurements, wherein the rotated measurements are combined to determine a net displacement, and wherein the navigational states comprise at least one of a geographic location, altitude, speed, heading, or orientation;
   and changing a power state of the accelerometer or gyroscope on the basis of a trigger event, wherein the trigger event is a change in navigational state.

9. The method of claim 8, wherein receiving the measurement information from the external sensor comprises:
   receiving measurement information from an external biomedical sensor.

10. The method of claim 9, wherein the biomedical sensor comprises a heart rate monitor.

11. The method of claim 9, wherein the biomedical sensor comprises a blood pressure monitor.

12. The method of claim 8, wherein the wireless interconnect comprises an interconnect implemented substantially according to a wireless standard.

13. The method of claim 8, wherein the wireless interconnect comprises an interconnect implemented substantially according to a near field communication standard.

14. The method of claim 8, further comprising:
   receiving, by the wireless interface unit, measurement information from an external processor.

15. A multi-sensor measurement processing unit, comprising:
   means for receiving, via an antenna, measurement information comprising satellite positioning system (SPS) measurements from an external sensor of a mobile station via a wireless interconnect;
   means for estimating one or more navigational of the multi-sensor measurement processing unit based on the measurement information and data from an accelerometer and a gyroscope disposed within a device incorporating the multi-sensor processing unit, wherein the accelerometer data comprise x-axis, y-axis, and z-axis data, wherein the gyroscope data comprise roll, pitch, and yaw data, wherein the gyroscope data is used to determine how much the multi-sensor measurement processor unit has rotated relative to a previous orientation to determine rotated measurements, wherein the rotated measurements are combined to determine a net displacement, wherein the navigational states comprise at least one of a geographic location, altitude, speed, heading, or orientation;
   and means for changing a power state of the accelerometer or gyroscope on the basis of a trigger event, wherein the trigger event is a change in navigational state.

16. The multi-sensor measurement processing unit of claim 15, wherein the means for receiving the measurement information from the external sensor comprises:
   means for receiving measurement information from an external biomedical sensor.

17. The multi-sensor measurement processing unit of claim 16, wherein the biomedical sensor comprises a heart rate monitor.

18. The multi-sensor measurement processing unit of claim 16, wherein the biomedical sensor comprises a blood pressure monitor.

19. The multi-sensor measurement processing unit of claim 15, wherein the wireless interconnect comprises an interconnect implemented substantially according to a wireless standard.

20. The multi-sensor measurement processing unit of claim 15, wherein the wireless interconnect comprises an interconnect implemented substantially according to a near field communication standard.

21. The multi-sensor measurement processing unit of claim 15, further comprising:
means for receiving measurement information from an external processor.

22. A non-transitory computer readable storage medium comprising computer instructions that, when executed on one or more processors, cause operations comprising:
receiving, via an antenna, by a wireless interface unit of a multi-sensor measurement processing unit comprising one or more sensors, measurement information comprising satellite positioning system (SPS) measurements from an external sensor of a mobile station via a wireless interconnect;
estimating one or more navigational states of the multi-sensor measurement processing unit based on the measurement information and from an accelerometer and a gyroscope disposed within a device incorporating the multi-sensor processing unit, wherein the accelerometer data comprise x-axis, y-axis, and z-axis data, wherein the gyroscope data comprise roll, pitch, and yaw data, wherein the gyroscope data is used to determine how much the multi-sensor measurement processor unit has rotated relative to a previous orientation to determine rotated measurements, wherein the rotated measurements are combined to determine a net displacement, wherein the navigational states comprise at least one of a geographic location, altitude, speed, heading, or orientation;
and changing a power state of the accelerometer or gyroscope on the basis of a trigger event, wherein the trigger event is a change in navigational state.

23. The non-transitory computer readable storage medium of claim 22, wherein receiving the measurement information from the external sensor comprises:
receiving measurement information from an external biomedical sensor.

24. The non-transitory computer readable storage medium of claim 23, wherein the biomedical sensor comprises a heart rate monitor.

25. The non-transitory computer readable storage medium of claim 23, wherein the biomedical sensor comprises a blood pressure monitor.

26. The non-transitory computer readable storage medium of claim 22, wherein the wireless interconnect comprises an interconnect implemented substantially according to a wireless standard.

27. The non-transitory computer readable storage medium of claim 22, wherein the wireless interconnect comprises an interconnect implemented substantially according to a near field communication standard.

28. The non-transitory computer readable storage medium of claim 22, further comprising additional computer instructions that cause additional operations comprising:
receiving, by the wireless interface unit, measurement information from an external processor.

* * * * *